United States Patent [19]

Ilg et al.

[11] Patent Number: 4,871,752
[45] Date of Patent: Oct. 3, 1989

[54] USE OF ARYLOXYCARBOXYLIC ACID DERIVATIVES AGAINST DERMATOLOGICAL DISEASES

[76] Inventors: Laszlo Ilg, Zermatter Strasse 29, 2800 Bremen 41, Fed. Rep. of Germany; Mario Gligora, A. Kovacica 22a, 5100 Rijeka, Yugoslavia

[21] Appl. No.: 68,100

[22] Filed: Jun. 30, 1987

[30] Foreign Application Priority Data

Jun. 30, 1986 [DE] Fed. Rep. of Germany ....... 3621861

[51] Int. Cl.$^4$ .................... A61K 31/44; A61K 31/235
[52] U.S. Cl. .................................... 514/355; 514/533; 514/534; 514/543; 514/860; 514/863; 514/928
[58] Field of Search ................ 514/533, 534, 355, 543

[56] References Cited

U.S. PATENT DOCUMENTS 3,262,850 7/1966 Jones et al. ..................... 514/567 X
3,769,431 10/1973 Grant et al. .......................... 514/543
4,310,512 1/1982 Schleppnik ..................... 514/543 X

*Primary Examiner*—Leonard Schenkman
*Attorney, Agent, or Firm*—Sughrue, Mion, Zinn, Macpeak & Seas

[57] ABSTRACT

The use of aryloxycarboxylic acid derivatives for the production of a medicament against dermatological diseases especially for combatting ulcus cruris, striae distense atrophicae, cellulitis, collagenoses (lupus erythematosus, sclerodermia, dermatomyositis etc.), REM-syndrome (reticular erythematus-syndrome), alopecia mucinosa, necrobiosis lipoidica diabeticorum, paniculitis nodosa, folliculitis decalvans, psoriasis vulgaris, elastosis senilis, disorders and diseases of elastic fibers, and mesenchymal tumors, collagenous and vascular diseases of the kidneys, liver and lungs, muscle diseases, mesenchymal tumors, burns, cicatrix, lichen sclerosus and atrophicans, anetodermiae (atrophiae cutis), immunological diseases, etc. and as an antagonist against corticosteroids is described.

3 Claims, No Drawings

USE OF ARYLOXYCARBOXYLIC ACID DERIVATIVES AGAINST DERMATOLOGICAL DISEASES

DESCRIPTION

The invention relates to the use of aryloxycarboxylic acid derivatives for the production of a medicament against dermatological diseases, especially for combatting striae distense atrophicae, ulcus cruris, cellulitis, REM-syndrome (reticular erythematos-syndrome), alopecia mucinosa, necrobiosis lipoidica diabeticorum, paniculitis nodosa, folliculitis decalvans, psoriasis vulgaris, and mesenchymal tumours, cicatrix, immunological diseases and as an antagonist for corticosteroids.

In DE-OS 36 06 041 the use of aryloxycarboxylic acid derivatives for controlling effluvium oleosum capilicium, i.e. hair loss due to excessive fat at the point of attachment of the hair, is described. Here, the drug is worked directly onto the lipocytes or matrix and bulb of the hair without thus causing damaging side effects.

Fat synthesis occurs in the lipocytes. Groups of lipocytes form "nodules" (globuli). The nodules are surrounded with collagen and reticular fibres. This capillary system serves to transfer the fat from the cells to the blood. Numerous lipogenic and lipobiotic factors have an influence on the lipocytes in the subcutis.

The lipocytes mainly produce triglycerides which are mainly derived from palmitic acid, stearic acid and unsaturated fatty acids. The fat ratios in the lipocytes resemble those in blood plasma. By topical application of lipid-lowering materials from the group aryloxycarboxylic acid derivatives a lasting improvement of hair condition could be achieved without the appearance of unwanted side-effects.

Similar disorders in fat and sebaceous metabolism occur in a series of dermatological diseases, such as especially cellulitis, paniculitis nodosa, psoriasis vulgaris, alopecia mucinosa, REM-syndrome (reticular erythematos-syndrome), folliculitis decalvans, necrobiosis lipoidica diabicorum, mesenchymal tumours, cicatrix. The aryloxycarboxylic acid derivatives may also be used an antagonists against corticosteroids.

In the case of striae distense atrophicae a decrease of elastic fibres can be detected in histological tests. The epidermis is atrophic. The epidermal annexes are missing. There is no skin pattern or hairs in the striae; as well as this the striae are situated under the level of healthy skin. It is known that collagen and lipocytes develop from the same mesenchymal cells in the embryonic phase. Thus, the need for a preparation arises that has an effect on the lipocytes and at the same time leads to a decrease of excess fat.

The object of the present invention is to suggest the use of a medicament that may be used in a simple manner for, and is better suited to, combatting dermatological diseases, especially the symptoms outlined above, as well as ulcus cruris and others, than medicaments used until now, in that it acts directly on disorders of the surrounding fat tissue. Of particular importance here is that it does not lead to the appearance of side-effects.

This object is achieved according to the invention by the use of aryloxycarboxylic acid derivatives that are suitable for combatting dermatological diseases, especially ulcus cruris, cellulitis, collagenoses (lupus erythematosus, sclerodermia, dermatomyositis etc.), striae distense atrophicae, REM-syndrome (reticular erythematus-syndrome), alopecia mucinosa, necrobiosis lipoidica diabeticorum, paniculitis nodosa, follucilitis decalvans, psoriasis vulgaris, elastosis senilis, disorders and diseases of elastic fibers, and mesenchymal tumours, collagenous and vascular diseases of the kidneys, liver and lungs, muscle disorders, mesenchymal tumours, burns, cicatrix, lichen sclerosus and atrophicans, anetodermiae (atrophiae cutis), immunological diseases etc. and as antagonist against corticosteroids.

The medicaments used according to the invention are suitable for all changes caused by diseases of the mesenchyme, independent of the organ and etiology, such as e.g. ulceration in the nasopharyngeal cavity, mouth ulcers, oesophageal ulcers and stomach ulcers. Among the medicaments having lipid-lowering activity taken from the group of aryloxycarboxylic acid derivatives, especially aryloxyacetic acid derivatives, which are suitable for combatting effluvium oleosum capilitium are to be understood compounds having the general formula

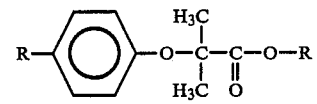

The substituents R may have the meanings given below. The corresponding derivatives are commercially available as known medicaments.

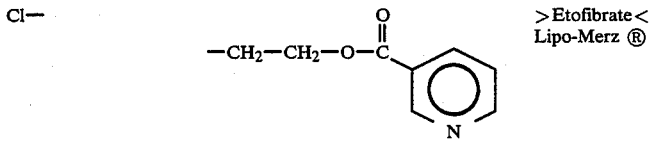

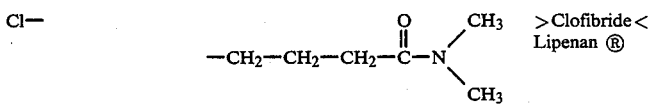

-continued

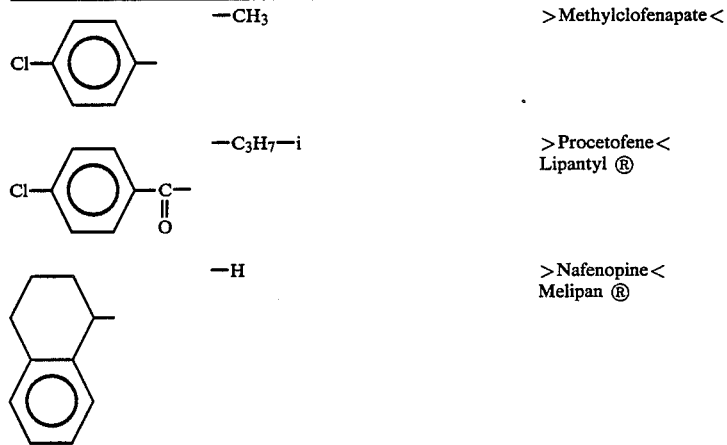

| | | |
|---|---|---|
| | —CH₃ | >Methylclofenapate< |
| | —C₃H₇—i | >Procetofene<<br>Lipantyl ® |
| | —H | >Nafenopine<<br>Melipan ® |

Two further esters of clofibrinic acid with symmetrical bifunctional alcohols should also be named. In the simfibrate the alcohol component is 1,3-propandiol; in the tiafibrate the tiadenol molecule component is contained:

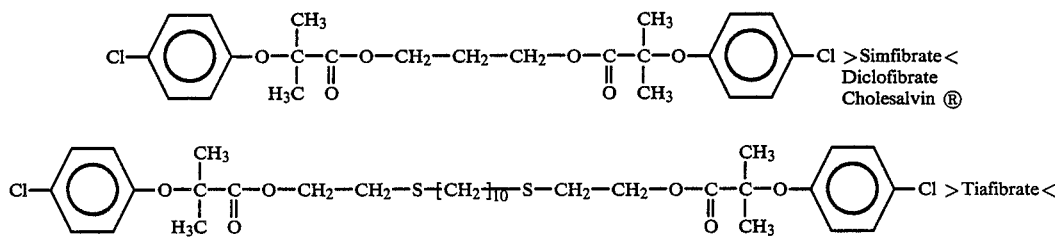

Further compounds preferably used according to the invention are fenofibrate (2-methyl-2-[4-(4-chlorobenzoyl)phenoxy]-propionic acid-isopropylester) as well as acetofilinfibrate.

It is known from the use of the above named lipid-lowering agents for the treatment of hyperlipidemia that they noticeably lower the cholesterol level and especially the content of triglyceride in the blood. Additionally, a reduction of the free fatty acid content is observed.

The above named lipid-lowering substances are topically applied onto the scalp as an alcoholic solution or as a suspension in alcohol, especially ethanol or isopropyl alcohol as well as spiritus dilutus, the solutions being 0.5 to 5%, preferably 0.5 to 3% solutions. It is preferred to apply the solution one to three times daily, especially preferably twice daily, the application suitably being achieved by means of a cottonwool swab.

It is also preferred to formulate the active ingredient as a 2 to 4%, preferably 2% gel (e.g. glycerine gel) or as a 3 to 5% salve (vaselinum album).

In order to further optimize the activity of the lipid-lowering agent containing solution, suspension, gel or salve, it is preferred to add vitamins to the solution or suspension, the positive effect of the vitamins on hair growth and fat metabolism already being known. Of particular note here are vitamin A, vitamin B, especially vitamin B₆ which has an antipruritic effect, vitamin D, vitamin E and/or vitamin K. The quantity of vitamins to be added to the solution or suspension to be used according to the invention is defined by the clinical situation requiring treatment. The vitamin amounts given in the following illustrate the preferred ranges:

| | |
|---|---|
| vitamin A | 200–2000 I.U. to 100 ml<br>most preferred 500–1000 I.U. |
| vitamin B<br>especially B₆ | 0.01–0.1%<br>most preferred 0.25% |
| vitamin D | 100–500 I.U. to 100 ml<br>especially preferred 200 I.U. |
| vitamin E | 0.005–0.1%<br>especially preferred 0.01% |

In addition to this it is advantageous for the improvement of the agent used according to the invention to add dexapanthenol (D-(+)-2,4-dihydroxy-3,3-dimethyl-N-(3-hydroxypropyl)-butyramide or panthenol. By means of the named substances an increased depth effect of the preparation can be achieved. The above named substances are preferably added to a concentration of 0.0005 to 0.01% and especially preferably in an amount of 0.001%.

It is further preferred to add an antibiotic to the solution, suspension, gel or salve used according to the invention. Neomycin, gentamycin, and erythromycin are especially suitable antibiotics. The antibiotics are added in an amount of 0.05 to 2%, especially preferably 0.5 to 1%, to the solution, suspension, gel or salve used according to the invention.

In addition to this cortisone can be added to the solution, suspension, gel or salve to be used according to the invention in a suitable amount, e.g. 0.1 to 2%.

The medicaments used according to the invention which contain derivatives of the aryloxycarboxylic acids can be administered topically, parenterally, subcutaneously or intrarectally. Topical application of the same is especially preferred. In the following a solution of a pharmaceutical formulation to be used according to the invention is given:

| | |
|---|---|
| clofibrate | 1% |
| dexapanthenol | 0.01% |
| vitamin A | 500 I.U. |
| vitamin B6 | 0.25% |
| vitamin D | 200 I.U. |
| vitamin E | 0.01% |
| sterilized water | remainder |

The following trials describe the use according to the invention:

1. Treatment of striae distense

The striae distensae cutis are ca. 15 mm long, sometimes wavy stripes running parallel which are initially reddish or purplish, later reddish-white or yellowish in hue, seldom hyperpigmented. The slightly sunken skin is weak, delicate, transversely folded, and also occasionally protruding in a hernia-like manner. On stretching it shows increased gloss. The striae are mostly found in the lumbosacral region, the thigh, the trochanter, and the suprapatellar region as well as the abdomen and breast. They mostly occur in puberty (in 70% of girls and 40% of boys) and in 90% of pregnancies in the last trimester. They are more common in whites than in blacks. Histologically, an atrophic epidermis is to be seen; the collagen is completely homogenized. The elastic fibres are fragmented, and form triangular foci with subpapillary bases and the apices in the subcutis. At the edge of these foci the elastic fibres are normal and often piled up. From the histogenesis of the skin we know that the fibroblasts develop from the mesenchyme. The fibroblasts produce the precursors of collagen and elastic fibres. The therapy with vitamins and massages used up until now was largely unsuccessful. For treatment of striae distensae therapy with a 2% glycerine-clofibrate-gel was used. In this way a direct effect on the diseased state of the mesenchyme should be achieved.

The therapy was carried out daily apart from Sundays in up to 20 sittings each lasting 5 to 20 minutes.

The following groups were treated:

1. 12 female patients with striae on the abdomen. They were treated with the above named gel with use of ultrasound (5 minutes; 0.8 to 1.0 W/cm$^2$).

2. 16 female patients with striae on the thighs. They were also treated with the above named gel with use of ultrasound (10 to 20 minutes; 0.6 to 0.8 W/cm$^2$).

3. 1 female patient with striae on the buttocks. She was treated with the above named gel in conjunction with ultrasound (8 to 10 minutes; 0.8 to 1.0 W/cm$^2$).

Results:

With the use of glycerine-clofibrate-gel without ultrasound a decrease of the striae was achieved, they became narrower. With additional ultrasound a quicker effect was achieved. The striae became narrower; some striae of up to 3 cm length disappeared completely. The skin in the surrounding area became more elastic.

After the treatment it could be ascertained that the striae returned to the same level as the skin. A normal skin pattern is achieved and lanugos rarely appear. The colour of the striae changes; they are no longer white but have a yellow sheen. It is known that collagen gives healthy skin a yellow sheen. This means that macroscopic collagen can already be detected. Histological investigations give the following:

Under the still atrophic epidermis the formation of a wave-formed boundary is observed and papillae can faintly be detected. New collagen is visible subepidermally. The elastic fibres are still discontinuous, i.e., lacerated, but increased. The collagen in the deap corium is also improved.

2. Treatment of ulcus cruris

For the following investigations preparations containing clofibrate and fenofibrate as active ingredients were used. The application was carried out locally for ulcus cruris of various etiology, such as postthrombotic ulcers, posttraumatic ulcers, triphic ulcers, arterial ulcers and necrosis lipoidica diabeticorum. The concentration of the active ingredient was 0.5 to 5%, especially 4% at the start of treatment and was later 2 to 3%. The medicament was administered either as a gel or in salve form.

The age of the patients was between 47 and 81. At the start of the treatment the disease was 3 months to 3 years old.

The size of the ulcers was between the size of a 10-West-German Pfennigs piece and the size of a hand with mainly sharply cut edges of varying depths. The form of the ulcers was very variable (round, long, irregularly bizarre). The base of the ulcers was covered with a fatty nectrotic film.

The best results were achieved with a combination treatment in which at the beginning a 4% gel or a corresponding salve and later a 2% gel (or salve) were applied. At the low concentrations a slow healing of the wound was observed. With use of a 5% gel there was hypertrophic granulation in the region of the base of the ulcers without a tendency to epithelialization. With simultaneous use of cortisone salves the hypertrophic granulation tissue disappeared.

At the start of the treatment the gel or salve was applied onto the wound three times daily and later, after the base of the ulcer had risen to the level of its surroundings, twice daily. The granulation of the base was usually accompanied by epithelialization at the edge but seldom with island-like epithelialization in the ulcers.

There was epithelialization in all the 16 patients treated. For half the patients (8) there was complete healing within 2½ months. For the remainder a clear tendency towards healing was observed. In summary it can be said that for all patients a positive effect could be observed from the medicament.

Bacteriologal investigations were carried out on all patients in two-weekly intervals. At the start of treatment only one type of bacteria could be detected. In the later stages of treatment up to three different types of bacteria were observed. Healing of the wound was not interrupted by this.

A histological investigation of four patients was carried out before and after the therapy in which tissue from the edge of the ulcers was removed:

Histological results before therapy with derivatives of the aryloxycarboxylic acids: Over the base of the ulcer fibrin with isolated necrotic cell remains are found. Under the ulcers non-specific granulation tissues without collagen are to be seen.

Histological results after therapy with derivatives of the aryloxycarboxylic acids: The epidermis is raised with numerous cells which are in a state of mitosis. In the corium there are granulation tissues with newly formed collagen fibres as well as newly formed capillary vessels with somewhat enlarged endothelial cells and hyperchromatic cell nuclei.

Therapy of the ulcus cruris with the derivatives of the aryloxycarboxylic acid led to good results on all patients. We did not observe any sensitivity with locally applied medicament in any patient.

3. Treatment of cellulitis (with ultrasound)

Cellulitis treatment with the aid of a 1% clofibrate solution was carried out on 20 female patients; a good result was achieved.

4. Treatment of psoriasis

It is known that in the case of psoriasis the lipid content in the scales is around 35% higher than in normal skin.

In this case a 3 to 5% salve was used over which a bandage was applied. It was shown that the scales disappeared more quickly due to the effect of glycerine-clofibrate-gel than when a placebo was used. With the aid of the active ingredient the first success could already be demonstrated after six days. Without further treatment there was a relapse. It can be deduced from this that use of the salve is particularly appropriate in combination with a corticosteroid or a similar preparation.

5. Treatment of folliculitis decalvans

This very rare disease was treated in a female patient with the aid of 2% clofibrate solution. After 20 days of treatment there was already renewed hair growth in the alopetic region; in methods of treatment up till now an irreversible hair loss always occurred.

6. Treatment of alopecia mucinosa and REM-syndrome

Treatment with 1% clofibrate solution showed itself to be successful in the case of alopecia mucinosa; there was new hair growth, and the oedematously infiltrated inflamed, reddened foci receded. Scaling ceased.

7. Treatment of necrobiosis lipoidica diabeticorum

Treatment with 1% clofibrate solution or acetofilinfibrate solution was used here. The therapy was successful. The erythma and oedema receded.

8. Treatment of mesenchymal tumours (multiple lipomas) (with ultrasound)

A female patient with multiple lipomas was treated with 3% of clofibrate-glycerine-gel and ultrasound. After 20 treatments it was established that the lipoma were softer and less conspicuous.

What is claimed is:

1. A method for treating a dermatological disease selected from the group consisting of striae distense, ulcus cruris, cellulitis, psoriasis, folliculitis decalvans, alopecia mucinosa, necrobiosis lipoidica diabeticorum and mesenchymal tumors which comprises topically, parenteral, subcutaneously or intrarectally administering to a patient a dermatological disease treating effect amount of an aryloxycarboxylic acid derivative selected from the group consisting of

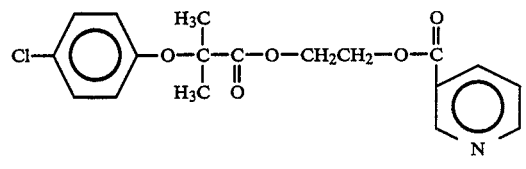

(Etofibrate)

and

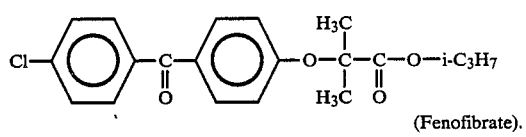

(Fenofibrate).

2. Method according to claim 1 wherein ulcus cruris is treated.

3. Method according to claim 1 in which vitamin A, B, especially $B_6$, D, E and/or K are further administered.

* * * * *